United States Patent [19]

Bates

[11] Patent Number: 4,704,280

[45] Date of Patent: Nov. 3, 1987

[54] COSMETIC LOTION

[76] Inventor: Harry L. Bates, 311 West Ave., Elmira, N.Y. 14904

[21] Appl. No.: 943,710

[22] Filed: Dec. 19, 1986

[51] Int. Cl.$^4$ .......................... A61K 7/06; A61K 7/48
[52] U.S. Cl. ................................. 424/195.1; 514/54; 514/847; 424/69
[58] Field of Search ...................... 424/69, 195.1, 847; 514/54

[56] References Cited

U.S. PATENT DOCUMENTS

| | | |
|---|---|---|
| 2,155,361 | 4/1939 | Meyers . |
| 2,602,039 | 7/1952 | Wershaw . |
| 3,137,622 | 6/1964 | Mueller et al. . |
| 3,360,511 | 12/1967 | Farkas . |
| 3,784,685 | 1/1974 | Kalopissis et al. . |
| 3,826,834 | 7/1974 | Reiches . |
| 4,201,235 | 5/1980 | Ciavatta . |
| 4,214,000 | 7/1980 | Papa . |
| 4,229,430 | 10/1980 | Fahim et al. . |
| 4,369,180 | 1/1983 | Mihalovitz . |
| 4,505,902 | 3/1985 | Millard . |
| 4,518,614 | 5/1985 | Parkinson . |
| 4,529,587 | 7/1985 | Green . |
| 4,547,364 | 10/1985 | Brown . |
| 4,584,191 | 4/1986 | Hostettler . |

Primary Examiner—John F. Terapane
Assistant Examiner—Susan Wolffe
Attorney, Agent, or Firm—L. Rita Quatrini

[57] ABSTRACT

A cosmetic lotion is disclosed consisting essentially of active components of from about 1 g to about 30 g of aloe vera, from about 30 mg to about 900 mg of zinc, about 100 mg to about 6000 mg of vitamin C, from about 25,000 USP Units to about 500,000 USP Units of vitamin A, from about 200 IU to about 4000 IU of vitamin E, from about 100 mg to about 2000 mg of vitamin B-6, from about 600 mcg to about 12,000 mcg of biotin, and from about 3 g to about 15 g of fruit pectin, per about 3 ounces of lotion. The balance is carriers and solvents. The zinc is supplied as one or more therapeutic compounds of zinc.

12 Claims, No Drawings

COSMETIC LOTION

This invention relates to a cosmetic lotion suitable for application to the skin.

BACKGROUND OF THE INVENTION

There are numerous skin preparations on the market today which are designed to soften the skin. However, up to this time I have not found a suitable preparation for especially rough and dry skin such as skin on the face which results from repeated shaving over a period of time causing rough hair stubble. Besides the more obvious effects of unattractiveness, redness, irritation, and sometimes infection, etc., this problem makes it extremely difficult to get a close shave and a number of razor blades are used in the process.

It would be desirable therefore to have a skin preparation which is so effective in softening the skin that even skin which is subjected to repeated shaving becomes softer as a result.

SUMMARY OF THE INVENTION

In accordance with one aspect of this invention there is provided a cosmetic lotion consisting essentially of the active components of from about 1 g to about 30 g of aloe vera, from about 30 mg to about 900 mg of zinc, about 100 mg to about 6000 mg of vitamin C, from about 25,000 USP Units to about 500,000 USP Units of vitamin A, from about 200 IU to about 4000 IU of vitamin E, from about 100 mg to about 2000 mg of vitamin B-6, from about 600 mcg to about 2,000 mcg of biotin, amd from about 3 g to about 15 g of fruit pectin, per about 3 ounces of lotion. The balance is carriers and solvents. The zinc is supplied as one or more therapeutic compounds of zinc.

DETAILED DESCRIPTION OF THE INVENTION

For a better understanding of the present invention, together with other and further objects, advantages and capabilities thereof, reference is made to the following disclosure and appended claims in connection with the above description of some of the aspects of the invention.

This invention relates to a cosmetic lotion which is especially useful for application to the skin. I have found that when this combination of ingredients is applied to the skin, for example in the form of a lotion, there results a softening of the skin. This softening effect is especially noticeable when applied to skin which has been roughened over time due to repeated shaving such as face and legs. I have also found that this cosmetic preparation when applied to the hair in small amounts leaves the hair soft without being greasy.

The cosmetic lotion of my invention consists essentially of the following active components in the following formulation:

| Component | Minimum Amount | Maximum Amount |
| --- | --- | --- |
| Aloe vera | 1 g | 30 g |
| Zinc | 30 mg | 900 mg |
| Vitamin C | 100 mg | 6000 mg |
| Vitamin A | 25,000 USP Units | 500,000 USP Units |
| Vitamin E | 200 IU | 4000 IU |
| Vitamin B-6 | 100 mg | 2000 mg |
| Biotin | 600 mcg | 12,000 mcg |
| Fruit pectin (dry basis) | 3 g | 15 g | per 3 ounces of lotion, with the balance being carriers and solvents.

A preferred formulation of the active components is given below per 3 ounces of the lotion:

| Component | Minumum Amount | Maximum Amount |
| --- | --- | --- |
| Aloe vera | 5 g | 20 g |
| Zinc | 60 mg | 600 mg |
| Vitamin C | 500 mg | 4500 mg |
| Vitamin A | 30,000 USP Units | 200,000 USP Units |
| Vitamin E | 250 IU | 2000 IU |
| Vitamin B-6 | 200 mg | 1500 mg |
| Biotin | 800 mcg | 9,000 mcg |
| Fruit pectin | 5 g | 12 g |

A more preferred formulation of the active components is given below per 3 ounces of the lotion:

| Component | Minimum Amount | Maximum Amount |
| --- | --- | --- |
| Aloe vera | 6 g | 10 g |
| Zinc | 90 mg | 300 mg |
| Vitamin C | 1000 mg | 3000 mg |
| Vitamin A | 40,000 USP Units | 100,000 USP Units |
| Vitamin E | 300 IU | 1000 IU |
| Vitamin B-6 | 300 mg | 1000 mg |
| Biotin | 1000 mcg | 6,000 mcg |
| Fruit pectin | 7 g | 10 g |

Most preferably the formulation of the active components is as follows per 3 ounces of the lotion:

| Component | Amount |
| --- | --- |
| Aloe vera | 6 g |
| Zinc | 180 mg |
| Vitamin C | 2000 mg |
| Vitamin A | 50,000 USP Units |
| Vitamin E | 400 IU |
| Vitamin B-6 | 400 mg |
| Biotin | 3000 mcg |
| Fruit pectin (dry basis) | 7.5 g |

The preferred solvent and carrier is water, preferably distilled water because of its purity.

The preparation can be made by any method which results in the components being uniformly blended, without departing from the scope of the invention.

In accordance with a preferred embodiment, the active components in the desired amounts are mixed with distilled water to a total volume of about 3 ounces. The amounts of active components which have been given for a total of about 3 ounces of lotion, can be adjusted proportionately depending on the total amount of lotion which is to be prepared. For example, for a total of about 6 ounces of the lotion, the amounts of the active components would be double the amounts given, and the solvents and carriers would be added to give a total of about 6 ounces of the lotion. Or, for about 1½ ounces of the lotion, the amounts of the active components would be about one-half the amounts given for the 3 ounces, and the solvents and carriers would be added to give a total of about 1½ ounces of the lotion.

In actuality, any source of aloe vera can be used as there are a number of preparations available today. Also the juice and/or gel from the aloe vera plant can be used. I prefer to use a preparation of aloe vera gel which is about 99.6% by weight aloe vera as the source of aloe vera.

Vitamin C can be used in the form of ascorbic acid or an ascorbate such as sodium ascorbate which is available commercially as a powder or in tablets.

The zinc is supplied in the form of one or more therapeutic zinc compounds. The term "therapeutic" as used in this invention in reference to zinc compounds means zinc compounds which can be used without harmful effects or which are considered non-poisonous. These compounds can be any such preparation available today such as zinc oxide, zinc salts, and preferably organic zinc compounds such as zinc gluconate.

The source of biotin based compounds can be biotin itself or biotin in a chemically bound form.

The source of vitamin B-6, can be pyridoxine, pyridoxol, pyridoxamine, or any source.

The source of fruit pectin can be any source available. However for ease of handling I prefer to use a commercial preparation of solubilized fruit pectin supplied by General Foods under the trade name of "Certo". When fruit pectin is used in a solubilized form, the liquid portion of the solubilized fruit pectin preparation becomes part of the solvents and carriers portion of the lotion.

The source of vitamin A can be any source available and this can be the water soluble form or in the form of an oil.

The source of vitamin E, tocopherol, is preferably predominately alpha tocopherol.

It is to be understood that in addition to the above named components, the preparation can contain other ingredients, for example, fragrances, colorants, preservatives, emulsifiers etc. without departing from the scope of the invention. An example of preservatives which can be used are propylparaben and TENOX BHA, the latter being a trademark of Eastman Chemical Products, Inc. for food grade antioxidants. BHA stands for butylated hydroxyanisole. The addition of these additional components does not detract from the basic benefits of the present invention and they can be present in minor amounts. The total amount of these additional components is preferably no greater than about 5% by weight of the total preparation.

While there has been shown and described what are at present considered the preferred embodiments of the invention, it will be obvious to those skilled in the art that various changes and modifications may be made therein without departing from the scope of the invention as defined by the appended claims.

What is claimed is:

1. A cosmetic lotion consisting essentially of active components in the following formulation per 3 ounces of lotion:

| Component | Minimum Amount | Maximum Amount |
| --- | --- | --- |
| Aloe vera | 1 g | 30 g |
| Zinc | 30 mg | 900 mg |
| Vitamin C | 100 mg | 6000 mg |
| Vitamin A | 25,000 USP Units | 500,000 USP Units |
| Vitamin E | 200 IU | 4000 IU |
| Vitamin B-6 | 100 mg | 2000 mg |
| Biotin | 600 mcg | 12,000 mcg |
| Fruit pectin | 3 g | 15 g | with the balance being carriers and solvents, and the zinc being supplied as one or more therapeutic zinc compounds.

2. A cosmetic lotion of claim 1 having additional components selected from the group consisting of preservatives, colorants, emulsifiers, fragrances and combinations thereof.

3. A cosmetic lotion of claim 1 wherein the solvent and carrier is water.

4. A cosmetic lotion of claim 1 wherein the active components are in the following formulation:

| Component | Minumum Amount | Maximum Amount |
| --- | --- | --- |
| Aloe vera | 5 g | 20 g |
| Zinc | 60 mg | 600 mg |
| Vitamin C | 500 mg | 4500 mg |
| Vitamin A | 30,000 USP Units | 200,000 USP Units |
| Vitamin E | 250 IU | 2000 IU |
| Vitamin B-6 | 200 mg | 1500 mg |
| Biotin | 800 mcg | 9,000 mcg |
| Fruit pectin | 5 g | 12 g |

5. A cosmetic lotion of claim 4 having additional components selected from the group consisting of preservatives, colorants, emulsifiers, fragrances and combinations thereof.

6. A cosmetic lotion of claim 4 wherein the solvent and carrier is water.

7. A cosmetic lotion of claim 4 wherein the active components are in the following formulation:

| Component | Minimum Amount | Maximum Amount |
| --- | --- | --- |
| Aloe vera | 6 g | 10 g |
| Zinc | 90 mg | 300 mg |
| Vitamin C | 1000 mg | 3000 mg |
| Vitamin A | 40,000 USP Units | 100,000 USP Units |
| Vitamin E | 300 IU | 1000 IU |
| Vitamin B-6 | 300 mg | 1000 mg |
| Biotin | 1000 mcg | 6,000 mcg |
| Fruit pectin | 7 g | 10 g |

8. A cosmetic lotion of claim 7 having additional components selected from the group consisting of preservatives, colorants, emulsifiers, fragrances and combinations thereof.

9. A cosmetic lotion of claim 7 wherein the solvent and carrier is water.

10. A cosmetic lotion of claim 7 wherein the active components are in the following formulation:

| Component | Amount |
| --- | --- |
| Aloe vera | 6 g |
| Zinc | 180 mg |
| Vitamin C | 2000 mg |
| Vitamin A | 50,000 USP Units |
| Vitamin E | 400 IU |
| Vitamin B-6 | 400 mg |
| Biotin | 3000 mcg |
| Fruit pectin (dry basis) | 7.5 g |

11. A cosmetic lotion of claim 10 having additional components selected from the group consisting of preservatives, colorants, emulsifiers, fragrances and combinations thereof.

12. A cosmetic lotion of claim 10 wherein the solvent and carrier is water.

* * * * *